United States Patent
Wakabayashi

(10) Patent No.: US 11,369,344 B2
(45) Date of Patent: Jun. 28, 2022

(54) ULTRASOUND TRANSDUCER AND ULTRASOUND ENDOSCOPE

(71) Applicant: OLYMPUS CORPORATION, Tokyo (JP)

(72) Inventor: Katsuhiro Wakabayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 177 days.

(21) Appl. No.: 16/796,095

(22) Filed: Feb. 20, 2020

(65) Prior Publication Data

US 2020/0187903 A1 Jun. 18, 2020

Related U.S. Application Data

(63) Continuation of application No. PCT/JP2018/039353, filed on Oct. 23, 2018.

(30) Foreign Application Priority Data

Oct. 24, 2017 (JP) .............................. JP2017-205432

(51) Int. Cl.
*A61B 8/00* (2006.01)
*A61B 8/12* (2006.01)
(Continued)

(52) U.S. Cl.
CPC ............... *A61B 8/445* (2013.01); *A61B 8/12* (2013.01); *A61B 8/4494* (2013.01); *H04R 17/00* (2013.01);
(Continued)

(58) Field of Classification Search
CPC ......... A61B 8/445; A61B 8/12; A61B 8/4494; A61B 1/00082; A61B 1/00114;
(Continued)

(56) References Cited

U.S. PATENT DOCUMENTS

2007/0293762 A1 12/2007 Sawada et al.
2014/0276069 A1* 9/2014 Amble ................. A61B 8/5207
600/447
2017/0303893 A1* 10/2017 Sato ....................... A61B 1/005

FOREIGN PATENT DOCUMENTS

CN 107205726 A 9/2017
JP 2847575 B2 1/1999
(Continued)

OTHER PUBLICATIONS

International Search Report dated Jan. 22, 2019 issued in PCT/JP2018/039353.
English Abstract of JP H04-166139 A, dated Jun. 12, 1992.

*Primary Examiner* — Joseph M Santos Rodriguez
*Assistant Examiner* — Kaitlyn E Sebastian
(74) *Attorney, Agent, or Firm* — Scully, Scott, Murphy & Presser, PC.

(57) ABSTRACT

An ultrasound transducer includes: a tube; a transducer cable which is fixed to an end portion side of the tube and close to an outer periphery of the tube; a plurality of piezoelectric elements which are arranged along a circumferential direction surrounding a central axis of the tube to face an outer peripheral surface of the tube, each piezoelectric element being configured to output an ultrasound wave according to an electric signal input from the transducer cable, and convert an ultrasound wave input from an external portion into an electric signal; and a plurality of relays which are electrically connected respectively to a plurality of signal lines included in the transducer cable and the plurality of piezoelectric elements, the relays being configured to relay the plurality of signal lines and the plurality of piezoelectric elements.

15 Claims, 10 Drawing Sheets

(51) Int. Cl.
  *H04R 17/00* (2006.01)
  *A61B 1/00* (2006.01)
  *A61B 1/07* (2006.01)
(52) U.S. Cl.
  CPC ....... *A61B 1/00082* (2013.01); *A61B 1/00114* (2013.01); *A61B 1/07* (2013.01)
(58) Field of Classification Search
  CPC ......... A61B 1/07; A61B 8/56; A61B 1/00096; A61B 1/018; A61B 1/05; A61B 1/0669; H04R 17/00
  See application file for complete search history.

(56) References Cited

FOREIGN PATENT DOCUMENTS

JP    2006-094981 A    4/2006
WO   WO 2016/190101 A1   12/2016

* cited by examiner

1

ULTRASOUND TRANSDUCER AND ULTRASOUND ENDOSCOPE

CROSS-REFERENCE TO RELATED APPLICATION

This application is a continuation of PCT International Application No. PCT/JP2018/039353 filed on Oct. 23, 2018, which designates the United States, incorporated herein by reference, and which claims the benefit of priority from Japanese Patent Application No. 2017-205432, filed on Oct. 24, 2017, incorporated herein by reference.

BACKGROUND

1. Technical Field

The present disclosure relates to an ultrasound transducer and an ultrasound endoscope.

2. Related Art

In the related art, there has been known an electronically radial scanning type ultrasound transducer having a plurality of piezoelectric elements regularly arranged cylindrically, and radially transmitting and receiving an ultrasound wave (refer, for example, to JP 2847575 B).

The ultrasound transducer (ultrasound probe) described in the JP 2847575 B is provided with a columnar base, a plurality of piezoelectric elements (micro piezoelectric pieces) which have a reed shape, are firmly attached to a backing member and are arranged circumferentially on an outer peripheral surface of the base, and a flexible board.

Here, the flexible board has a connection area with the same width as an arrangement width of a plurality of piezoelectric elements in one end side thereof, and extends from the connection area toward the other end side with an expanded width. Further, the other end side of the flexible board is provided with a plurality of electrode lands which are electrically connected to a transducer cable. Further, the flexible board is wound in such a manner as to be partly overlapped in the other end side, the connection area is electrically connected to a plurality of piezoelectric elements and each of a plurality of electrode lands in the other end side is electrically connected to the transducer cable. More specifically, an electric signal from the transducer cable is input to a plurality of piezoelectric elements via the flexible board. As a result, each of a plurality of piezoelectric elements emits an ultrasound wave. Further, the electric signal input to a plurality of piezoelectric elements and converted by a plurality of piezoelectric elements is output to a transducer cable via the flexible board.

SUMMARY

In some embodiments, an ultrasound transducer includes: a tube which is constructed by using an insulating material; a transducer cable which is fixed to an end portion side of the tube and close to an outer periphery of the tube; a plurality of piezoelectric elements which are arranged along a circumferential direction surrounding a central axis of the tube to face an outer peripheral surface of the tube, each piezoelectric element being configured to output an ultrasound wave according to an electric signal input from the transducer cable, and convert an ultrasound wave input from an external portion into an electric signal; and a plurality of relays which are electrically connected respectively to a plurality of signal lines included in the transducer cable and the plurality of piezoelectric elements, the relays being configured to relay the plurality of signal lines and the plurality of piezoelectric elements. The signal lines are electrically connected to the relays on the outer peripheral surface of the tube, and are arranged toward a fixed position of the transducer cable from a partial area in a side of the fixed position among a whole circumference in the circumferential direction on the outer peripheral surface.

In some embodiments, an ultrasound endoscope includes: the ultrasound transducer; an objective optical portion which is inserted into an inner portion of the tube, the objective optical portion being configured to take in a subjective image; and a light guide which is inserted into the inner portion of the tube, the light guide being configured to guide an illumination light that irradiates a subject.

The above and other features, advantages and technical and industrial significance of this disclosure will be better understood by reading the following detailed description of presently preferred embodiments of the disclosure, when considered in connection with the accompanying drawings.

DETAILED DESCRIPTION

A description will be given below of modes for carrying out the disclosure (hereinafter, refer to as embodiments) with reference to the drawings. The disclosure is not limited by the embodiments described below. Further, same reference signs are attached to same portions in the description of the drawings.

First Embodiment

Schematic Structure of Endoscope System

Figure 1:
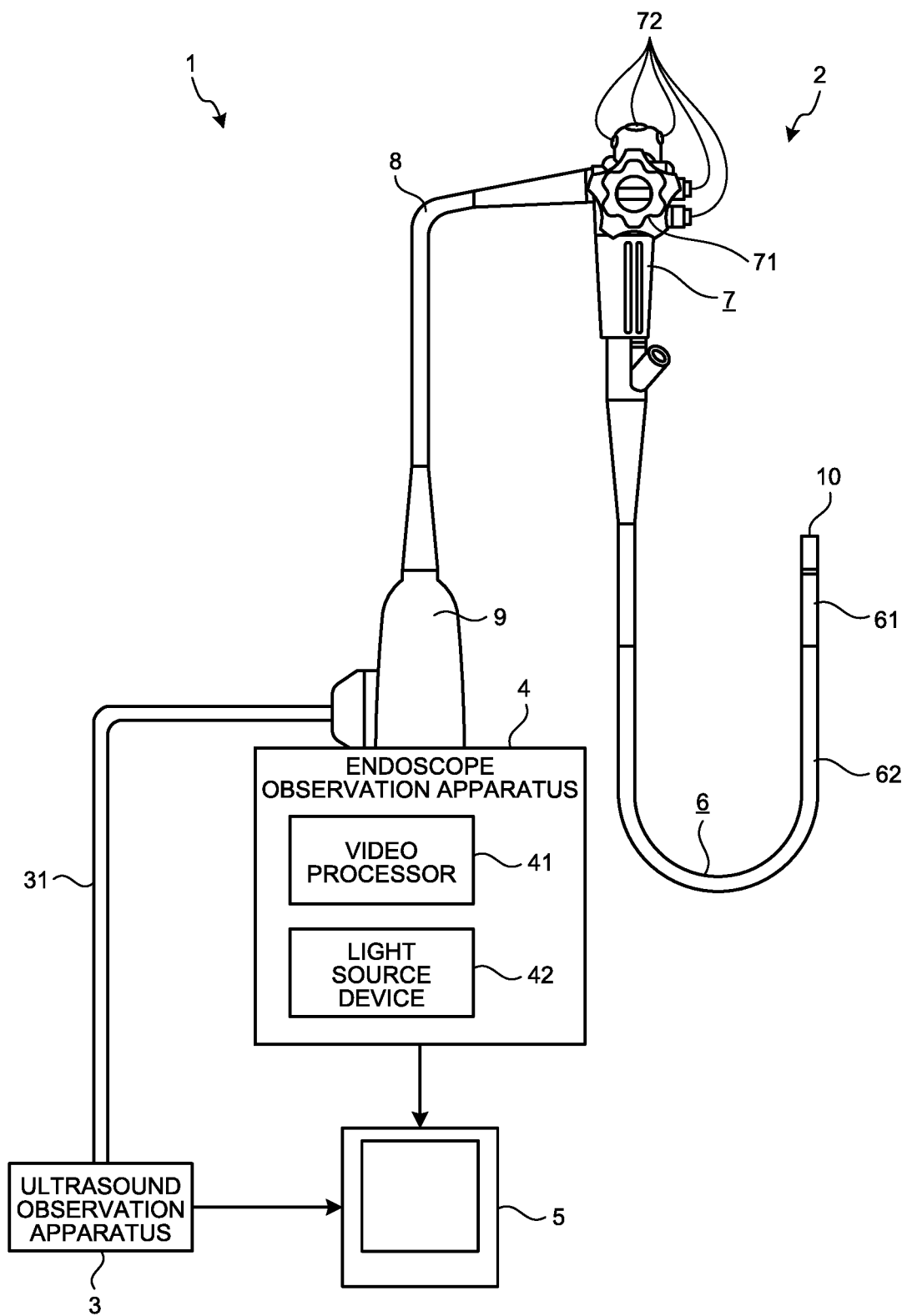
FIG. 1 is a view schematically illustrating an endoscope system according to a first embodiment.

FIG. 1 is a view schematically illustrating an endoscope system 1 according to a first embodiment.

The endoscope system 1 is a system which makes an ultrasound diagnosis in a subject such as human by using an ultrasound endoscope. The endoscope system 1 is provided with an ultrasound endoscope 2, an ultrasound observation apparatus 3, an endoscope observation apparatus 4 and a display device 5, as illustrated in FIG. 1.

The ultrasound endoscope 2 can be partly inserted into the subject, and has a function of transmitting an ultrasound pulse (acoustic pulse) toward a body wall in the subject and receiving an ultrasound echo reflected by the subject so as to output an echo signal, and a function of capturing an inner side of the subject and outputting an image signal.

A detailed structure of the ultrasound endoscope 2 will be mentioned later.

The ultrasound observation apparatus 3 is electrically connected to the ultrasound endoscope 2 via an ultrasound cable 31 (FIG. 1), outputs the pulse signal to the ultrasound endoscope 2 via the ultrasound cable 31 and inputs the echo signal from the ultrasound endoscope 2. Further, the ultrasound observation apparatus 3 applies a predetermined process to the echo signal and generates the ultrasound image.

A connector for endoscope 9 (FIG. 1) mentioned later of the ultrasound endoscope 2 is detachably connected to the endoscope observation apparatus 4. The endoscope observation apparatus 4 is provided with a video processor 41 and a light source device 42 as illustrated in FIG. 1.

The video processor 41 inputs the image signal from the ultrasound endoscope 2 via the connector for endoscope 9. Further, the video processor 41 applies a predetermined process to the image signal and generates the endoscope image.

The light source device 42 supplies illumination light illuminating the inner side of the subject via the connector for endoscope 9 to the ultrasound endoscope 2.

The display device 5 is constructed by using a liquid crystal or an organic electro luminescence (EL), and displays the ultrasound image generated by the ultrasound observation apparatus 3, and the endoscope image generated by the endoscope observation apparatus 4.

Structure of Ultrasound Endoscope

Next, a description will be given of a structure of the ultrasound endoscope 2.

The ultrasound endoscope 2 is provided with an insertion unit 6, an operating unit 7, a universal cord 8 and the connector for endoscope 9, as illustrated in FIG. 1.

The term "distal end side" described below means a distal end side of the insertion unit 6 (a distal end side in an inserting direction into the subject). Further, the term "proximal end side" described below means a side moving away from the distal end of the insertion unit 6.

The insertion unit 6 is a portion which is inserted into the subject. The insertion unit 6 is provided with an ultrasound transducer 10 which is provided at the distal end, a curved portion 61 which is connected to the proximal end side of the ultrasound transducer 10 and can be curved, and a flexible tube 62 which is connected to the proximal end side of the curved portion 61 and has a flexibility, as illustrated in FIG. 1.

A detailed structure of the ultrasound transducer 10 corresponding to a main part of the disclosure will be described later.

The operating unit 7 is a unit which is connected to the proximal end side of the insertion unit 6, and accepts various operations from a doctor and the like. The operating unit 7 is provided with a curve knob 71 for curving the curved portion 61, and a plurality of operating members 72 for making various operations, as illustrated in FIG. 1.

The universal cord 8 is a cord which extends from the operating unit 7, and is arranged a light guide 101 (refer to FIG. 3) transmitting the illumination light supplied from the light source device 42, a transducer cable 14 (refer to FIG. 3) transmitting the pulse signal and the echo signal mentioned above, and a signal cable 201 (refer to FIG. 3) transmitting the image signal mentioned above.

The connector for endoscope 9 is provided in an end portion of the universal cord 8. Further, the ultrasound cable 31 is connected to the connector for endoscope 9, and the connector for endoscope 9 connects to the video processor 41 and the light source device 42 by being inserted into the endoscope observation apparatus 4.

Structure of Ultrasound Transducer

Next, a description will be given of a structure of the ultrasound transducer 10.

Figure 2:
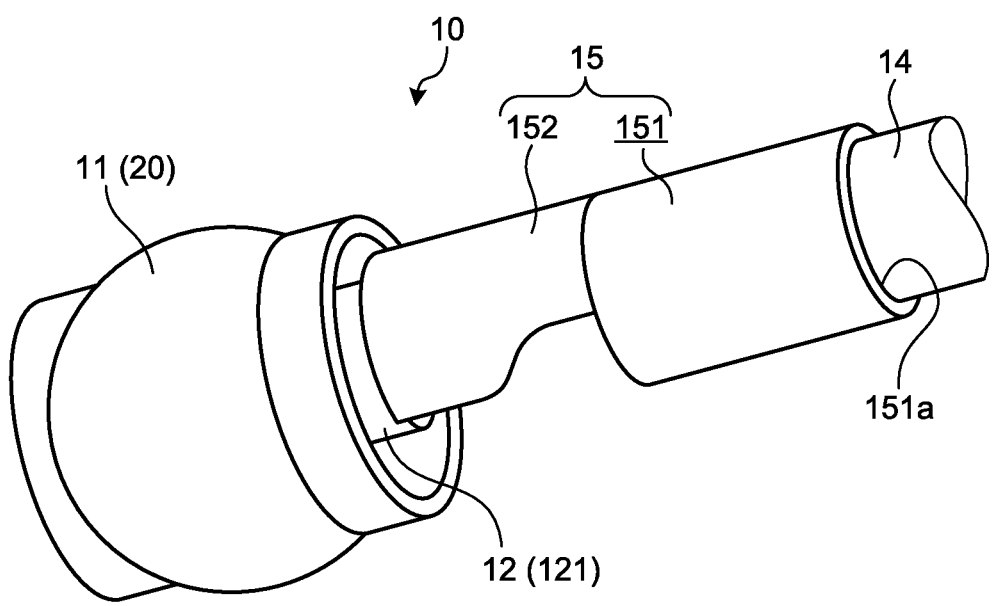
FIG. 2 is a view illustrating a structure of an ultrasound transducer.
Figure 3:
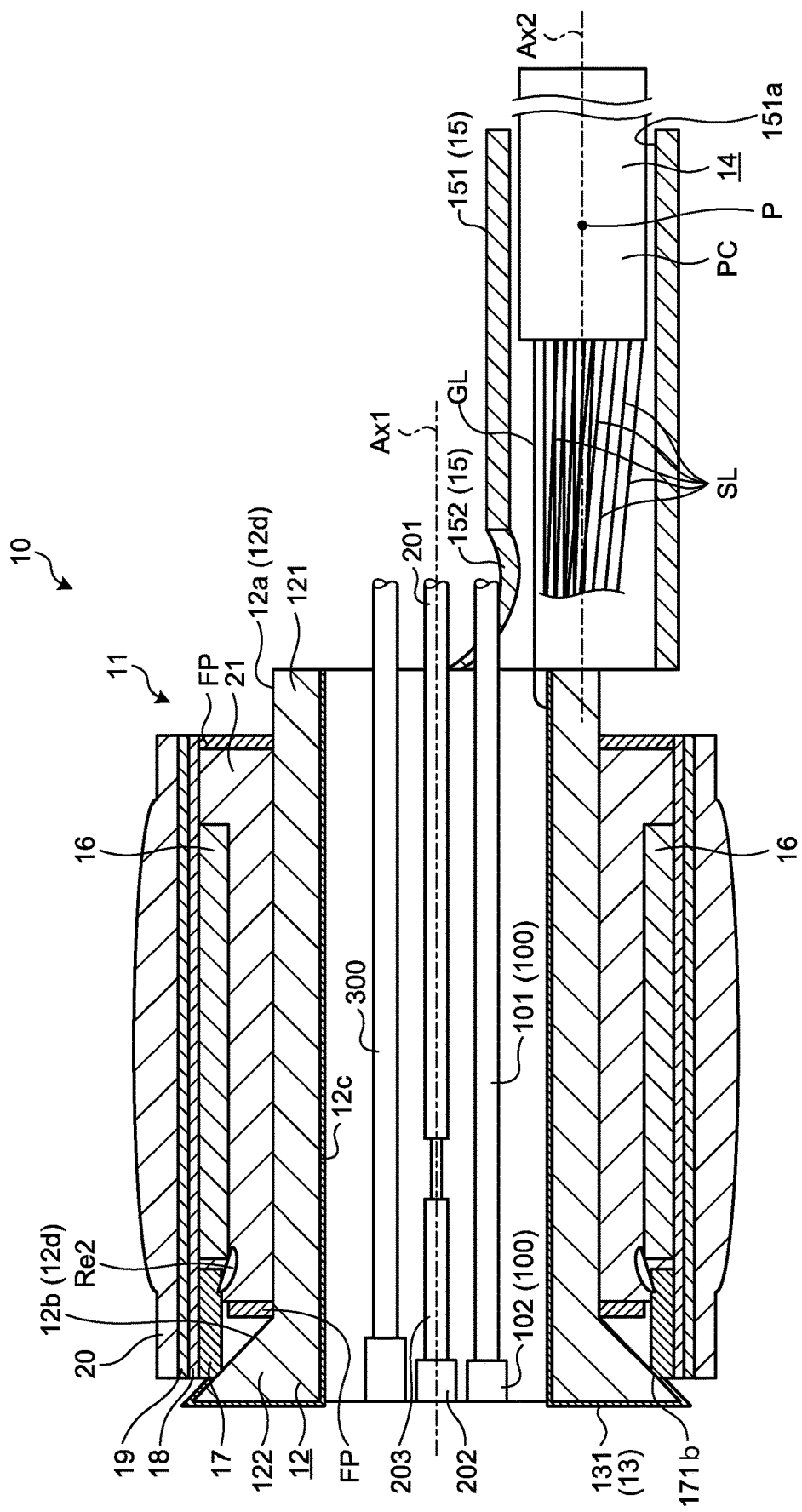
FIG. 3 is a view illustrating the structure of the ultrasound transducer.

FIGS. 2 and 3 are views illustrating the structure of the ultrasound transducer 10. Specifically, FIG. 2 is a perspective view obtained by viewing the ultrasound transducer 10 from the proximal end side. FIG. 3 is a cross sectional view obtained by cutting the ultrasound transducer 10 with a plane passing through a central axis Ax1 of an oscillator unit 11. In FIG. 3, an illustration of first and second electrodes 22 and 23, a groove unit for short circuit 181, a conductive resin Re1, first and second conductive layers 172 and 173 and a second wiring pattern 132 is omitted for convenience of description.

The ultrasound transducer 10 is an electronically radial scanning type ultrasound transducer, and has a plurality of piezoelectric elements 16 (FIG. 3) which are regularly arranged so as to form a cylinder. Further, the ultrasound transducer 10 radially sends the ultrasound pulse from the cylinder, and scans the ultrasound pulse in a rotating direction of 360 degree around the central axis Ax1 of the cylinder. The ultrasound transducer 10 is provided with an oscillator unit 11, a tube 12, a plurality of relays 13, a transducer cable 14, and a retention member 15, as illustrated in FIG. 2 or 3.

Figure 4:
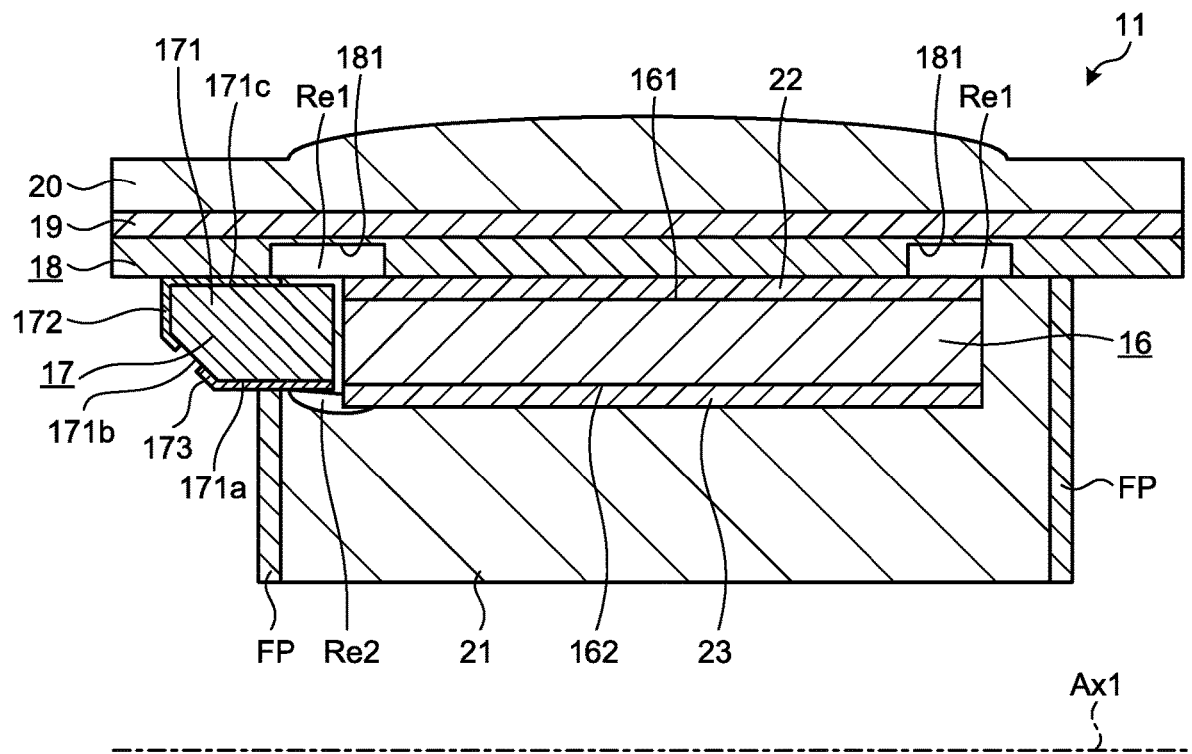
FIG. 4 is a view illustrating a structure of an oscillator unit.

FIG. 4 is a view illustrating the structure of the oscillator unit 11. Specifically, FIG. 4 is a view in which a part of FIG. 3 is enlarged.

The oscillator unit 11 is a unit in which a plurality of piezoelectric elements 16, a printed board 17, first and second acoustic matching layers 18 and 19, an acoustic lens 20 and a backing member 21 are integrated, as shown in FIG. 4, and has a cylindrical shape in which a direction along an inserting direction of the insertion unit 6 is set to the central axis Ax1.

A plurality of piezoelectric elements 16 are regularly arranged along a circumferential direction surrounding the central axis Ax1. The plurality of piezoelectric elements 16 all have the same shape, and each of them has a rectangular parallelepiped shape extending linearly along the central axis Ax1. Further, first and second electrodes 22 and 23 are formed on an outer surface of the piezoelectric element 16.

The first electrode 22 is a ground electrode which is constructed by a metal material or a resin material having a conductivity, and is formed on the following outer surface in the piezoelectric element 16.

More specifically, the first electrode 22 is formed approximately in a whole surface of a first surface 161 which is parallel to the central axis Ax1 and is positioned in an outer surface side (a side being away from the central axis Ax1) of the ultrasound transducer 10, on the outer surface of the piezoelectric element 16, as illustrated in FIG. 4.

The second electrode 23 is a signal electrode which is constructed by the metal material or the resin material having the conductivity, and is formed on the following outer surface in the piezoelectric element 16.

More specifically, the second electrode 23 is formed approximately on a whole surface of a second surface 162 which is positioned in an opposite side to the first surface 161, on the outer surface of the piezoelectric element 16, as illustrated in FIG. 4.

Further, the piezoelectric element 16 converts the pulse signal (corresponding to the electric signal according to the disclosure) input via the second electrode 23 into the ultrasound pulse and sends to the subject. Further, the piezoelectric element 16 converts the ultrasound echo reflected by the subject into an electric echo signal (corresponding to the electric signal according to the disclosure) expressed by a voltage change, and outputs.

Here, the piezoelectric element 16 is formed by using a PMN-PT single crystal, a PMN-PZT single crystal, a PZN-PT single crystal, a PIN-PZN-PT single crystal or a relaxer based piezoelectric material.

The PMN-PT single crystal is an abbreviated name of solid solutions of a lead magnesium niobate and a lead titanate. The PMN-PZT single crystal is an abbreviated name of solid solutions of the lead magnesium niobate and a lead zirconate titanate. The PZN-PT single crystal is an abbreviated name of solid solutions of a zinc lead niobate and a lead titanate. The PIN-PZN-PT single crystal is an abbreviated name of solid solutions of an indium lead niobate, a zinc lead niobate and the lead titanate. The relaxer based piezoelectric material is a collective term of three-component based piezoelectric materials obtained by adding a lead based complex perovskite corresponding to a relaxer material to a lead zirconate titanate (PZT) for the purpose of increasing a piezoelectric constant or a dielectric constant. The lead based complex perovskite is expressed by Pb (B1, B2) $O_3$, in which B1 is any one of magnesium, zinc, indium and scandium, and B2 is any one of niobium, tantalum and tungsten. These materials have an excellent piezoelectric effect. As a result, it is possible to make a value of an electric impedance low even if downsized, and it is preferable in the light of an impedance matching between the first and second electrodes 22 and 23.

The printed board 17 is a portion where the first and second electrodes 22 and 23 provided in each of the piezoelectric elements 16 are electrically connected respectively to all the relays 13. The printed board 17 is provided with a board 171, a first conductive layer 172 and a plurality of second conductive layers 173, as illustrated in FIG. 4.

The board 171 is a board which is constructed by an insulating material such as polyimide, and is formed into approximately the same cylindrical shape as a cylindrical shape which is formed by all the regularly arranged piezoelectric elements 16. Further, the board 171 is arranged in the distal end side in relation to the piezoelectric element 16.

In this board 171, a slope face 171b expanding toward the distal end side is formed in an edge portion of a distal end of a cylindrical inner peripheral surface 171a while copying an outer peripheral surface 12b (FIG. 3) of a flange portion 122 (FIG. 3) mentioned later in the tube 12, as illustrated in FIG. 4.

The first conductive layer 172 is a ground wiring which is electrically connected to the first electrode 22 corresponding to the ground electrode, and is formed on the following outer surface in the board 171.

More specifically, the first conductive layer 172 is formed so as to extend to the slope face 171b from a cylindrical outer peripheral surface 171c in the board 171 as illustrated in FIG. 4.

A plurality of second conductive layers 173 are signal wirings each of which is electrically connected to the second electrode 23 corresponding to the signal electrode provided in each of the piezoelectric elements 16, and are formed on the following outer surface in the board 171.

More specifically, a plurality of second conductive layers 173 are regularly arranged along a circumferential direction of the inner peripheral surface 171a, and are formed so as to extend to the slope face 171b from the inner peripheral surface 171a. The first and second conductive layers 172 and 173 are not in contact on the slope face 171b, and are spaced at such a distance that an insulation property between the first and second conductive layers 172 and 173 can be secured.

The first acoustic matching layer 18 is provided in an outer surface side of the ultrasound transducer 10 in relation to the piezoelectric element 16 and the printed board 17, and is formed into a cylindrical shape, as illustrated in FIG. 4. The second acoustic matching layer 19 is constructed by a different material from the first acoustic matching layer 18, is provided in an outer surface side of the ultrasound transducer 10 in relation to the first acoustic matching layer 18, and is formed into a cylindrical shape.

More specifically, the first and second acoustic matching layers 18 and 19 are members which match an acoustic impedance between the piezoelectric element 16 and the subject for efficiently transmitting sound (ultrasound wave) between the piezoelectric element 16 and the subject.

In the present first embodiment, the description is given on the assumption that the two-layers of first and second acoustic matching layers 18 and 19 are provided, however, the matching layer may be formed as one layer according to a property between the piezoelectric element 16 and the subject or may be formed as three or more layers. Further, the acoustic matching layer may be formed as an ultrasound transducer having no acoustic matching layer as long as the acoustic impedance is matched with the subject.

The acoustic lens 20 is constructed, for example, by using a silicone resin, has approximately a cylindrical shape in which an outer peripheral surface is curved into a convex shape as illustrated in FIG. 4, and is positioned on an outer surface of the oscillator unit 11 (the ultrasound transducer 10). Further, the acoustic lens 20 has a function of focusing the ultrasound pulses which are sent from the piezoelectric element 16 and pass through the first and second acoustic matching layers 18 and 19.

The oscillator unit 11 may be provided with or without the acoustic lens 20.

The backing member 21 is positioned in an inward side of the ultrasound transducer 10 in relation to the piezoelectric element 16 and the printed board 17, and is formed into a cylindrical shape. Further, the backing member 21 damps an unnecessary ultrasound oscillation which is generated by a motion of the piezoelectric element 16. The backing member 21 is formed by using a material having a great damping rate, for example, an epoxy resin obtained by dispersing a filler such as alumina or zirconia, or a rubber obtained by dispersing the filler mentioned above.

The oscillator unit 11 described above is manufactured, for example, as illustrated below.

First, a worker forms the first acoustic matching layer 18 on the flat second acoustic matching layer 19. Further, a groove unit for short circuit 181 (FIG. 4) is formed for the first acoustic matching layer 18 at each of positions which face both end portions in a longitudinal direction in the piezoelectric element 16. Further, the worker sets the first acoustic matching layer 18 to a finally necessary thickness by filling each of the groove units for short circuits 181 with a conductive resin Re1 (FIG. 4), and grinding together with the conductive resin Re1.

Next, the worker sticks the base material for the piezoelectric element onto the first acoustic matching layer 18 in a posture in which one plate surface (corresponding to the first surface 161) in a flat base material for piezoelectric element (not illustrated) faces the first acoustic matching layer 18.

Here, the base material for piezoelectric element is a flat plate which is formed by using a material constructing the piezoelectric element 16. Further, a first thin film (not illustrated) constructed by the same material as the first electrode 22 is formed on a whole of one plate surface (corresponding to the first surface 161) in the base material for piezoelectric element. Further, a second thin film (not illustrated) constructed by the same material as the second electrode 23 is formed on a whole of the other plate surface (corresponding to the second surface 162) in the base material for piezoelectric element. As a result, the first thin film electrically conducts the conductive resin Re1 filled in each of the groove units for short circuits 181 by sticking the base material for piezoelectric element onto the first acoustic matching layer 18 as mentioned above.

Next, the worker sticks the printed board 17 onto the first acoustic matching layer 18 in adjacent to the base material for piezoelectric element mentioned above in a posture in which one plate surface (corresponding to the outer peripheral surface 171c) in the flat printed board 17 faces the first acoustic matching layer 18. Further, the first conductive layer 172 electrically conducts the conductive resin Re1 filled in each of the groove units for short circuits 181 and electrically connects to the first thin film mentioned above by sticking the printed board 17 onto the first acoustic matching layer 18. Further, the worker electrically conducts all the second conductive layers 173 and the second thin film respectively with the conductive resin Ret (FIG. 4).

Next, the worker moves a blade of a precision cutting machine such as a dicing saw while rotating, and cuts the base material for piezoelectric element mentioned above. As a result, all the piezoelectric elements 16 are respectively formed, and the first and second thin films mentioned above are electrically separated, so that each of the first and second electrodes 22 and 23 is formed in each of the piezoelectric elements 16.

Next, the worker curves the cut unit mentioned above (the unit obtained by integrating the first and second acoustic matching layers 18 and 19, the piezoelectric element 16 and the printed board 17) into a cylindrical shape. Further, the worker separates a pair of annular flat plates FP (FIG. 4) forming a barrier when cast molding the backing member 21 in the longitudinal direction of the piezoelectric element 16 and firmly attaches them to a cylindrical inner side of the unit. Further, the worker pours a liquid backing member between a pair of flat plates FP, cast molds the liquid backing member while rotating the unit in a circumferential direction surrounding the cylindrical central axis Ax1 of the unit, and forms the cylindrical backing member 21 having a hole in a center portion thereof by heating and hardening.

Next, the worker puts the unit in which the backing member 21 is cast molded as mentioned above into a mold, fills the mold with a liquid resin material and hardens the resin material, thereby forming the acoustic lens 20 in an outer peripheral surface of the unit.

The oscillator unit 11 is manufactured by the above steps.

Figure 5:
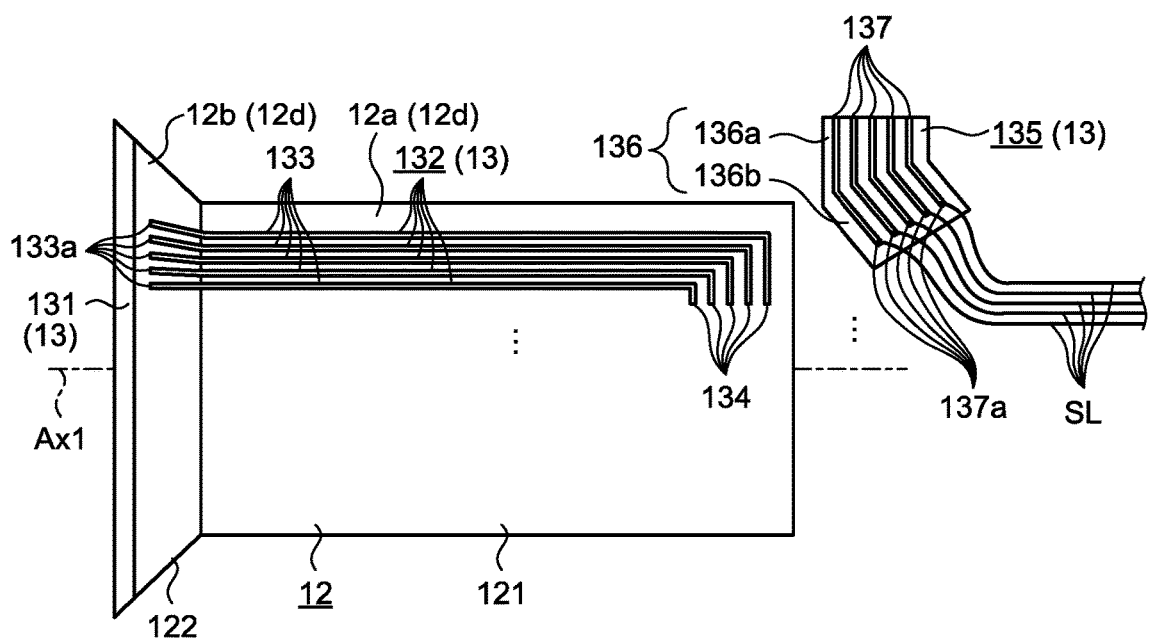
FIG. 5 is a view illustrating a structure of a tube.

FIG. 5 is a view illustrating a structure of the tube 12.

The tube 12 is constructed by using the insulating material. The tube 12 is provided with a tube main body 121 and a flange portion 122 as illustrated in FIG. 5.

The tube main body 121 is formed into a cylindrical shape having an outer diameter which is somewhat smaller than an inner diameter of the oscillator unit 11.

The flange portion 122 is provided at a distal end of the tube main body 121, and is a portion which protrudes from an outer peripheral surface 12a of the tube main body 121. More specifically, the flange portion 122 has a circular truncated cone shape which is expanded toward the distal end. A maximum diameter of an outer peripheral surface 12b of the flange portion 122 is set to be greater than the inner diameter of the cylindrical printed board 17.

A plurality of relays 13 are electrically connected to each of the first conductive layer 172 (the first electrode 22 per the piezoelectric element 16) and all the second conductive layers 173 (the second electrode 23 per the piezoelectric element 16), and the transducer cable 14. Further, a plurality of relays 13 relay each of the first conductive layer 172 and all the second conductive layers 173, and the transducer cable 14. Each of these plurality of relays 13 is provided with a first wiring pattern 131, a second wiring pattern 132 (FIG. 5) and a flexible board 135 (FIG. 5) as shown in FIG. 3 or 5. In the following description, the flexible board 135 is described as an FPC board 135 for convenience of description.

The first wiring pattern 131 is a ground wiring which electrically connects to the first conductive layer 172 (the first electrode 22 per the piezoelectric element 16), and is formed in the tube 12.

Specifically, the first wiring pattern 131 is formed so as to extend from the outer peripheral surface 12b of the flange portion 122 to the distal end side and extend to the proximal end of the tube 12 following an inner peripheral surface 12c of the tube 12, as illustrated in FIG. 3 or 5. Further, the first wiring pattern 131 is formed as a solid pattern over a whole periphery surrounding the central axis Ax1 of the tube 12 in a circumferential direction. Further, the first wiring pattern 131 is electrically connected to a ground line GL (FIG. 3) constructing the transducer cable 14 in the proximal end side of the tube 12.

A method of electrically connecting the first wiring pattern 131 and the first conductive layer 172 will be mentioned later.

The second wiring pattern 132 corresponds to the wiring pattern according to the disclosure, and the same number of the second wiring patterns 132 as that of the piezoelectric elements 16 (the second electrodes 23) are provided. These plurality of second wiring patterns 132 are signal wirings which are electrically connected respectively to all the second conductive layers 173 (the second electrodes 23 per the piezoelectric element 16), and are respectively formed on an outer peripheral surface 12d of the tube 12 (the outer peripheral surface 12a of the tube main body 121 and the outer peripheral surface 12b of the flange portion 122). In the present first embodiment, all the second wiring patterns 132 are regularly arranged in the circumferential direction in which plural sets each including five second wiring patterns surround the central axis Ax1. Since all the sets of second wiring patterns 132 have the same shape, a description will be given below of one set of (five) second wiring patterns 132.

One set of (five) second wiring patterns 132 are arranged in the circumferential direction surrounding the central axis Ax1 on the outer peripheral surface 12d of the tube 12, as illustrated in FIG. 5. Each of these one set of (five) second wiring patterns 132 is provided with a pattern main body 133 and a bent portion 134.

The pattern main body 133 extends from the outer peripheral surface 12b of the flange portion 122 to the proximal end side, and extends to the proximal end side of the tube 12 approximately in parallel to the central axis Ax1 following the outer peripheral surface 12a of the tube main body 121. Each of the pattern main bodies 133 in one set of (five) second wiring patterns 132 is formed in such a manner that each of end portions in the distal end side is arranged in the circumferential direction surrounding the central axis Ax1, and each of end portions in the proximal end side is arranged at a position which is shifted in the direction of the central axis Ax1. Further, the first and second wiring patterns 131 and 132 are not in contact on the outer peripheral surface 12b of the flange portion 122, and are spaced at a distance which can secure an insulation property between the first and second wiring patterns 131 and 132.

The bent portion 134 is a portion which is bent approximately perpendicularly along the circumferential direction surrounding the central axis Ax1 from the end portion in the proximal end side of the pattern main body 133 and extends. Each of the bent portions 134 in one set of (five) second wiring patterns 132 is formed in such a manner that each of the end portions is arranged approximately in parallel to the central axis Ax1.

Further, the distal end side end portion in the pattern main body 133 serves as an element side connection portion 133a (FIG. 5) which is electrically connected to the second conductive layer 173 (the second electrode 23).

Figure 6:
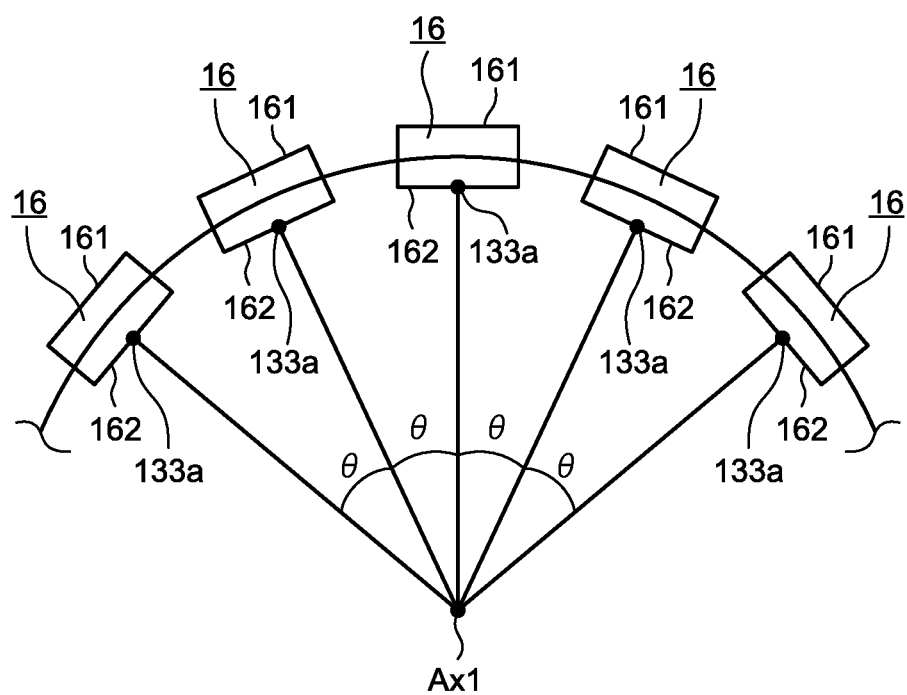
FIG. 6 is a view schematically illustrating a positional relationship between a piezoelectric element and an element side connection portion.

FIG. 6 is a view schematically illustrating a positional relationship between the piezoelectric element 16 and the element side connection portion 133a. Specifically, FIG. 6 is a view obtained by viewing the piezoelectric element 16 and the element side connection portion 133a from the direction along the central axis Ax1.

All the second wiring patterns 132 are set in such a manner that a pitch angle around the central axis Ax1 of each of the element side connection portions 133a is the same angle θ as a pitch angle around the central axis Ax1 in each of the piezoelectric elements 16, as illustrated in FIG. 6.

A method of electrically connecting the second wiring pattern 132 and the second conductive layer 173 will be mentioned later.

The FPC board 135 corresponds to the extended portion according to the disclosure, and the same number of FPC boards as that of the set of second wiring patterns 132 are provided. Each of the plurality of FPC boards 135 is provided with a board 136 and a plurality of (five in the present embodiment) conductive layers 137.

The board 136 is a flexible board which is constructed by an insulating material such as polyimide. The board 136 is provided with first and second extended portions 136a and 136b as illustrated in FIG. 5.

The first extended portion 136a is provided in one end side of the board 136 and extends in one direction.

The second extended portion 136b is provided in the other end side of the board 136 and extends in one direction from one end of the first extended portion 136a while being bent at a predetermined angle in relation to the extending direction of the first extended portion 136a.

Five conductive layers 137 are arranged in a width direction of the board 136, and each of them is formed so as to extend from one end side of the board 136 toward the other end side.

Figure 7:
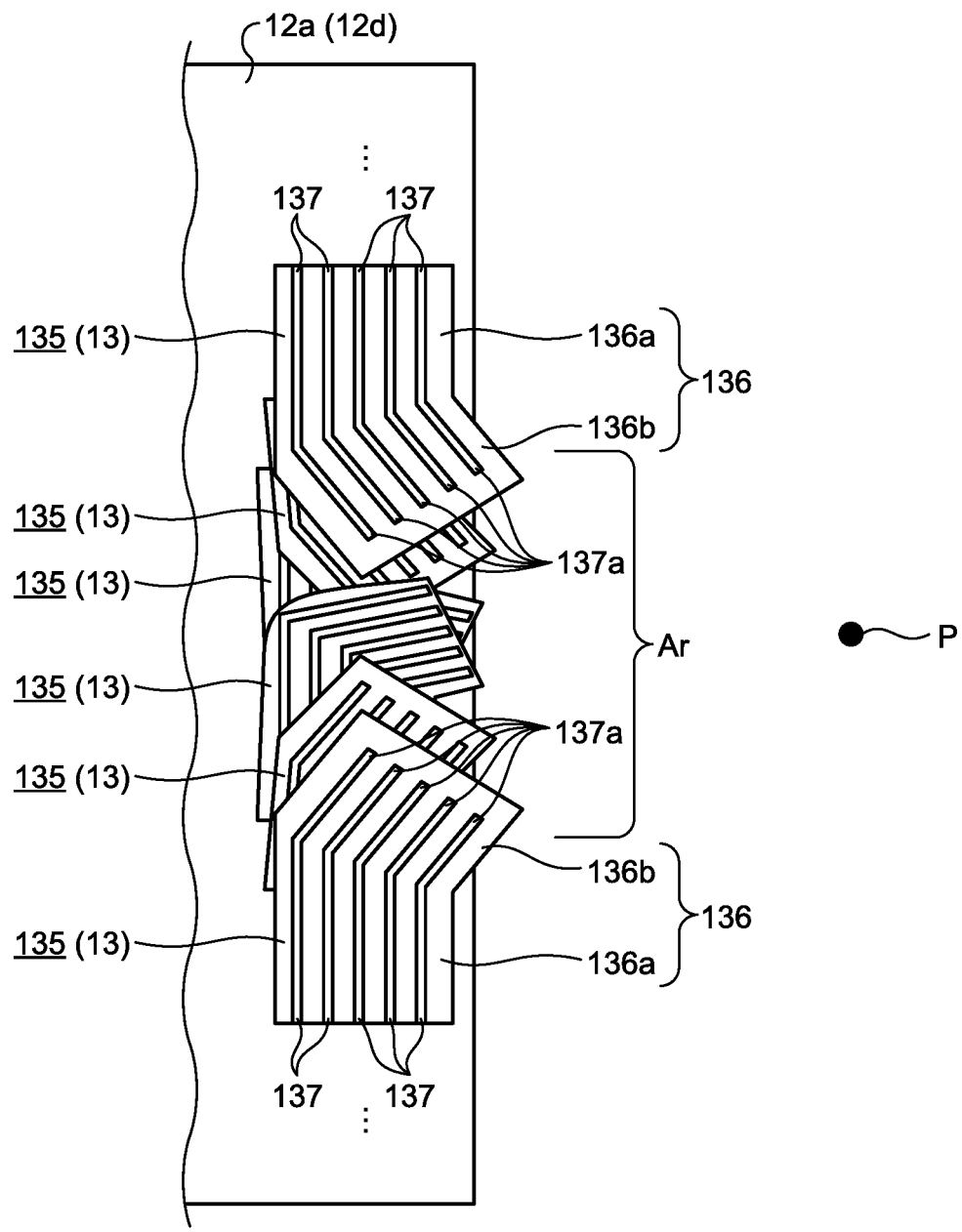
FIG. 7 is a view illustrating an extending direction of first and second extended portions.

FIG. 7 is a view illustrating the extending direction of the first and second extended portions 136a and 136b. Specifically, FIG. 7 is a view obtained by expanding a whole circumference in the circumferential direction surrounding the central axis Ax1 in the tube 12 into a plane in such a manner that an area Ar (a lower side area in FIG. 3) in a side where the transducer cable 14 is fixed in the whole circumference forms a center. In FIG. 7, an illustration of the second wiring pattern 132 is omitted for convenience of description.

Further, the FPC board 135 is stuck on the outer peripheral surface 12d of the tube 12 in such a manner that the extending direction of the first extended portion 136a is along a circumferential direction (a vertical direction in FIG. 7) surrounding the central axis Ax1, and the extending direction of the second extended portion 136b is directed to a fixed position P (FIGS. 3 and 7) of the transducer cable 14, as illustrated in FIG. 7. As a result, in five conductive layers 137, each of the end portions in one end side of the board 136 is electrically connected to each of the end portions of each of the bent portions 134 in one set of (five) second wiring patterns 132. Further, in five conductive layers 137, each of the end portions in the other end side of the board 136 corresponds to each of the cable side connection portions 137a (FIGS. 5 and 7) according to the disclosure, and is electrically connected to each of five signal lines SL (FIG. 5) constructing the transducer cable 14.

All the FPC boards 135 are set, as illustrate in FIG. 7, so as to be different in lengths of the first and second extended portions 136a and 136b and an angle at which the second extended portion 136b is bent in relation to the first extended portion 136a. Further, all the FPC boards 135 are stuck on the outer peripheral surface 12d of the tube 12 in an overlapping state in which at least a part of each of the second extended portions 136b is positioned in the area Ar, and the extending direction of each of the second extended portions 136b is directed to the fixed position P side. As a result, the signal line SL is electrically connected to the FPC board 135 on the outer peripheral surface 12d of the tube 12, and is routed toward the fixed position P from the partial area Ar in the fixed position P side of the transducer cable 14 among the whole circumference in the circumferential direction in the outer peripheral surface 12d.

Further, in the present first embodiment, the arranged direction of each of the element side connection portions 133a in one set of (five) second wiring patterns 132 is a circumferential direction surrounding the central axis Ax1. On the other hand, the arranged direction of each of the cable side connection portions 137a in the FPC board 135 is a direction which intersects in the circumferential direction surrounding the central axis Ax1. More specifically, the arranged direction of each of the element side connection portions 133a is set to be different from the arranged direction of each of the cable side connection portions 137a.

The transducer cable 14 is a so-called coaxial cable provided with the same number of signal lines SL as that of the piezoelectric elements 16, a dielectric layer (not illustrated) which coats the signal lines SL, a ground line GL (shield) which coats the dielectric layer, and a protective coating PC (FIG. 3) which coats the ground line GL and has an insulation property.

Figure 8:
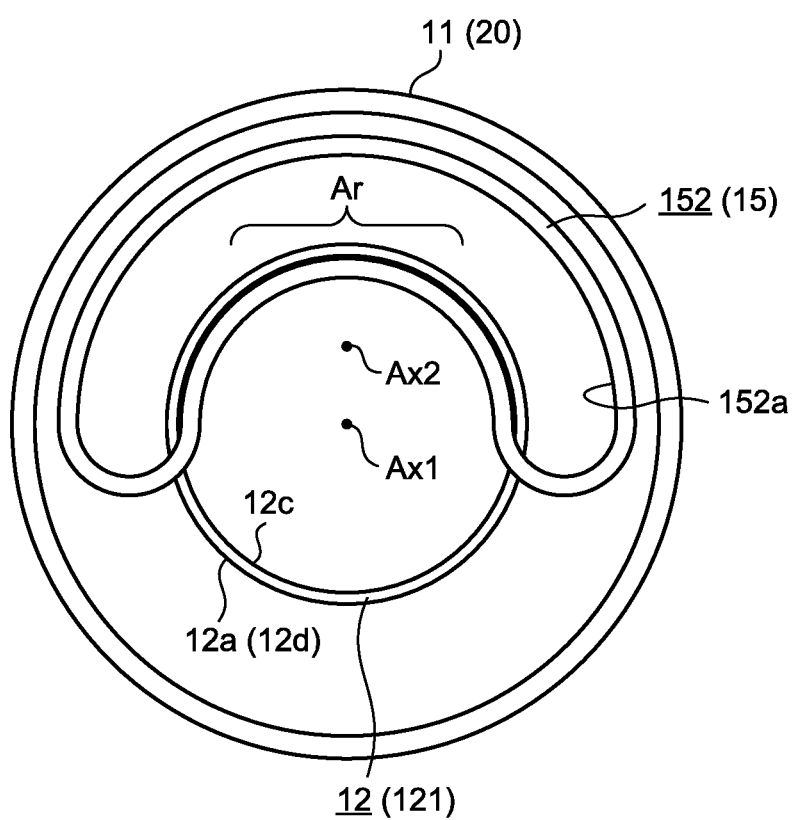
FIG. 8 is a view illustrating a structure of a retention member.

FIG. 8 is a view illustrating a structure of the retention member 15. Specifically, FIG. 8 is a view obtained by cutting the retention member 15 (a wiring coated portion 152) with an orthogonal plane to the central axis Ax1 and viewing from the proximal end side.

The retention member 15 is a member which is constructed by an insulating material and retains the transducer cable 14. The retention member 15 is provided with a retention member main body 151 (FIG. 2) and the wiring coated portion 152 as illustrated in FIG. 2 or 8.

The retention member main body 151 has a cylindrical shape having a first hole portion 151*a* into which the transducer cable 14 is inserted, and is a member which retains the transducer cable 14. More specifically, the fixed position P of the transducer cable 14 is positioned within the retention member main body 151 (FIG. 3).

The wiring coated portion 152 is formed in a partial area of a whole circumference in a circumferential direction surrounding a central axis Ax2 (FIGS. 3 and 8) of the retention member main body 151 in one end of the retention member main body 151. The wiring coated portion 152 has a circular arc shape in a cross sectional view and is formed into a tubular shape having a second hole portion 152*a* which extends along the central axis Ax2 of the retention member main body 151. The second hole portion 152*a* is communicated with the first hole portion 151*a*. Further, the wiring coated portion 152 coats each of the signal lines SL which are connected to all the FPC boards 135 and are routed to the fixed position P side, and the ground line GL which is connected to the first wiring pattern 131 and is routed to the fixed position P side.

The retention member 15 described above is fixed to the oscillator unit 11 via a fixing member (not illustrated) in a posture in which the second hole portion 152*a* faces the area Ar in the outer peripheral surface 12*d* of the tube 12. At this time, the central axis Ax2 does not meet the central axis Ax1 and is positioned closer to an outer periphery of the tube 12 in a parallel state to the central axis Ax1. More specifically, the transducer cable 14 retained by the retention member 15 is fixed to the proximal end side of the tube 12 and closer to an outer periphery.

In the present first embodiment, within the tube 12, as illustrated in FIG. 3, there are arranged an output end side of a light guide 101, an illumination lens 102 which irradiates the subject along the central axis Ax1 with an illumination light output from the output end of the light guide 101, an objective optical portion 202 which condenses the light (subject image) reflected in the subject, an imaging unit 203 which captures the subject image guided by the objective optical portion 202, and a treatment tool channel 300 for protruding a treatment tool along the central axis Ax1 from the distal end of the insertion unit 6. Further, the image signal captured by the imaging unit 203 is transmitted to the endoscope observation apparatus 4 (the video processor 41) via the signal cable 201. The light guide 101 and the illumination lens 102 correspond to the light guide 100 according to the disclosure.

More specifically, the ultrasound endoscope 2 according to the present first embodiment is constructed as a direct vision type endoscope which observes the direction along the central axis Ax1. The ultrasound endoscope 2 is not limited to the direct vision type endoscope, but may be constructed as a diagonal view type endoscope which observes a direction intersecting the central axis Ax1 at an acute angle, or a side view type endoscope which obverses an orthogonal direction to the central axis Ax1.

Method of Connecting First and Second Wiring Patterns and First and Second Conductive Layers Next, a description will be given of a method of electrically connecting the first and second wiring patterns 131 and 132 and the first and second conductive layers 172 and 173.

Figure 9:
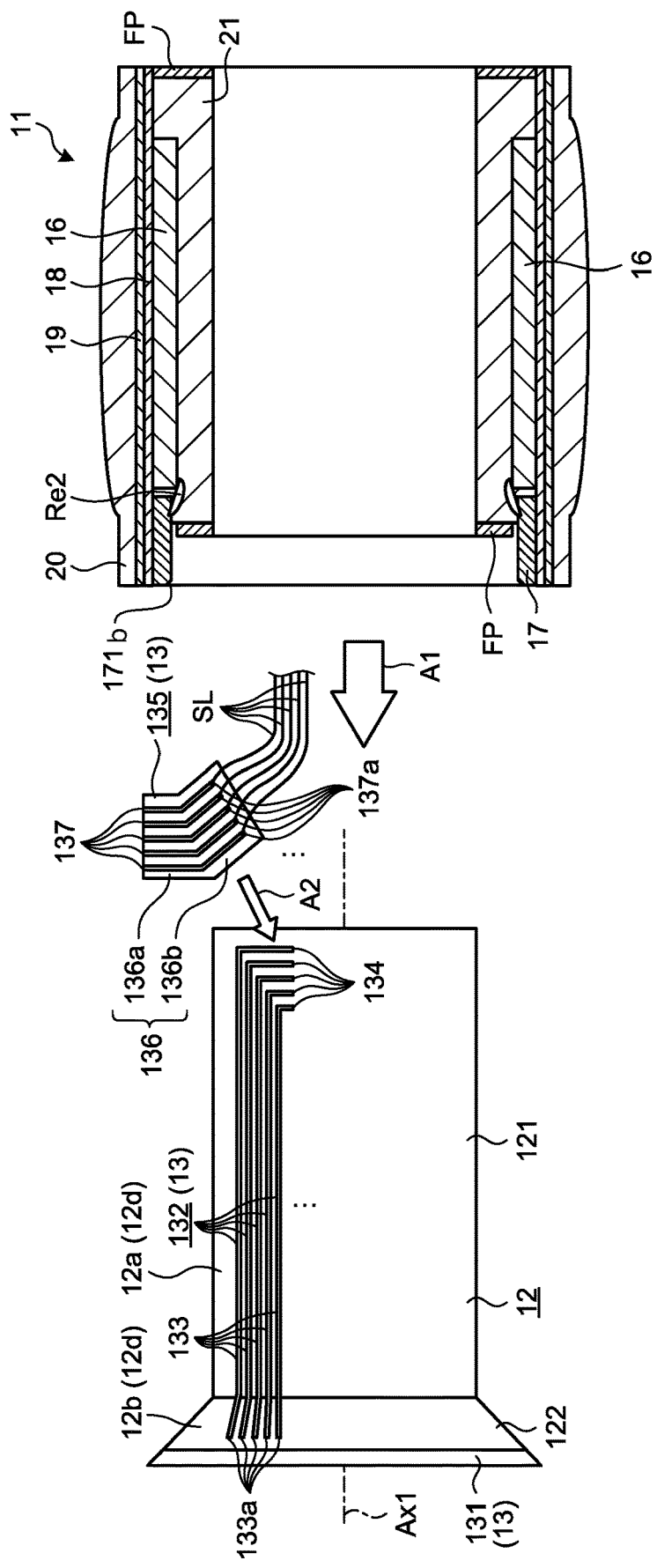
FIG. 9 is a view describing a method of connecting between first and second wiring patterns and first and second conductive layers.

FIG. 9 is a view describing the method of connecting the first and second wiring patterns 131 and 132 and the first and second conductive layers 172 and 173.

First, the worker applies an adhesive agent to the outer peripheral surface 12*d* of the tube 12.

Next, the worker adjusts rotational positions around the central axis Ax1 of the tube 12 (rotational positions of a plurality of element side connection portions 133*a* in relation to a plurality of second conductive layers 173), and inserts the proximal end side of the tube 12 into the oscillator unit 11 as shown by an arrow A1 in FIG. 9. Further, the worker applies the flange portion 122 to the slope face 171*b* of the printed board 17 and hardens the adhesive agent. As a result, the first and second wiring patterns 131 and 132 on the outer peripheral surface 12*b* of the flange portion 122 are electrically connected to the first and second conductive layers 172 and 173 on the slope face 171*b*, respectively.

Subsequently, the worker sticks all the FPC boards 135 to which all the signal lines SL of the transducer cable 14 are respectively connected, to the outer peripheral surface 12*d* of the tube 12, and electrically connects all the FPC boards 135 and all sets of second wiring patterns 132, as illustrated by an arrow A2 in FIG. 9. Further, the worker connects the ground line GL of the transducer cable 14 to the first wiring pattern 131.

Each of the steps mentioned above may be mechanically made by a manufacturing device without any manpower.

According to the present first embodiment described above, the following effects can be achieved.

In the ultrasound transducer 10 according to the present first embodiment, the signal line SL is electrically connected to the relay 13 on the outer peripheral surface 12*d* of the tube 12, and is routed toward the fixed position P from the partial area Ar in the fixed position P side of the transducer cable 14 among the whole circumference in the circumferential direction on the outer peripheral surface 12*d*. As a result, in comparison with the structure in which each of the signal lines SL constructing the transducer cable 14 is routed toward the fixed position P of the transducer cable 14 from the area over the whole circumference in the circumferential direction on the outer peripheral surface 12*d*, the fixed position P can be set to the position close to the tube 12. More specifically, it is possible to make the length of the signal line SL routed to the fixed position P from the outer peripheral surface of the tube 12 short by making the position between the tube 12 and the fixed position P short. Therefore, it is not necessary to make the tube 12 longer unnecessarily for the purpose of preventing the disconnection of the signal line SL.

Therefore, on the basis of the ultrasound transducer 10 according to the present first embodiment, there can be achieved an effect that the length of the tube 12 can be shortened and the rigid length can be shortened.

Further, in the ultrasound transducer 10 according to the present first embodiment, the relay 13 is provided with the FPC board 135 which extends along the circumferential direction surrounding the central axis Ax1 on the outer peripheral surface 12*d* of the tube 12 and electrically connects to the signal line SL by being bent and extending to the fixed position P side. As a result, the signal line SL can be easily routed toward the fixed position P from the partial area Ar on the outer peripheral surface 12*d* of the tube 12.

In particular, all the FPC boards 135 are stuck on the outer peripheral surface 12*d* of the tube 12 in an overlapping state together. As a result, the signal line SL can be easily routed toward the fixed position P from the area Ar by forming the second wiring pattern 132 in the wide area over the whole circumference of the outer peripheral surface 12d of the tube 12 and utilizing the FPC board 135.

Further, in the ultrasound transducer 10 according to the present first embodiment, each of the end portions of each of the bent portions 134 in one set of (five) second wiring patterns 132 is formed so as to be arranged approximately in parallel to the central axis Ax1. More specifically, since each of the end portions of each of the bent portions 134 is arranged linearly instead of the curved shape curved on the outer peripheral surface 12d of the tube 12, it is possible to easily make a sticking work of the FPC board 135.

Further, in the ultrasound transducer 10 according to the present first embodiment, the tube 12 is provided with the tube main body 121, and the flange portion 122 which protrudes from the outer peripheral surface 12a of the tube main body 121 and faces a plurality of piezoelectric elements 16 in the direction along the central axis Ax1. Further, the second wiring pattern 132 is provided across the outer peripheral surface 12a of the tube main body 121 and the outer peripheral surface 12b of the flange portion 122. Further, the pitch angle around the central axis Ax1 of each of the element side connection portions 133a and the pitch angle around the central axis Ax1 in each of the piezoelectric elements 16 are set to be the same angle θ. As a result, it is possible to easily connect electrically the second wiring pattern 132 and the second conductive layer 173 (the second electrode 23) only by adjusting the rotational position around the central axis Ax1 of the tube 12 and applying the flange portion 122 to the slope face 171b of the printed board 17. Further, since any heat is not utilized for bonding the second wiring pattern 132 and the second conductive layer 173 (the second electrode 23), a heat-labile piezoelectric element such as a single crystal can be utilized as the piezoelectric element 16, so that it is possible to improve a degree of freedom of design.

Second Embodiment

Next, a description will be given of the present second embodiment.

In the following description, same reference signs are attached to the same structures as those of the first embodiment mentioned above, and a detailed description thereof will be omitted or simplified.

Figure 10:
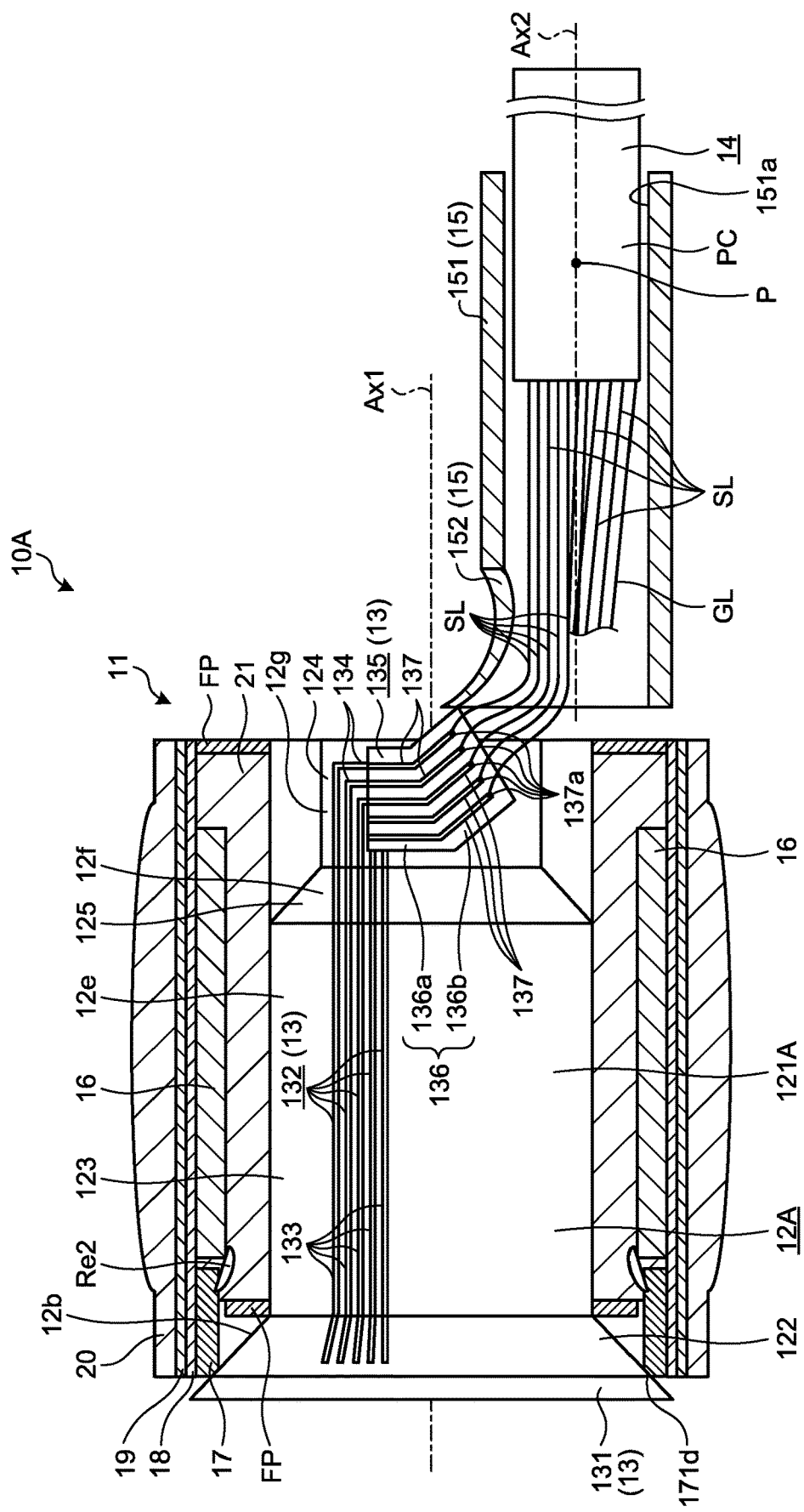
FIG. 10 is a view illustrating a structure of an ultrasound transducer according to a second embodiment.

FIG. 10 is a view illustrating a structure of an ultrasound transducer 10A according to the present second embodiment. Specifically, FIG. 10 is a cross sectional view corresponding to FIG. 3. In FIG. 10, a tube 12A is not cut for convenience of description.

The ultrasound transducer 10A according to the present second embodiment employs the tube 12A having a different shape from the tube 12 for the ultrasound transducer 10 (FIG. 3) described in the first embodiment mentioned above, as illustrated in FIG. 10.

The tube 12A employs a tube main body 121A having a different shape from the tube main body 121 for the tube 12 described in the first embodiment mentioned above.

The tube main body 121A is provided with a large diameter portion 123, a small diameter portion 124 and a connection portion 125 as illustrate in FIG. 10.

The large diameter portion 123 is positioned at a distal end of the tube main body 121A, has the same outer diameter as that of the tube main body 121 described in the first embodiment mentioned above, and has a shorter length than the tube main body 121.

The small diameter portion 124 corresponds to the stepped portion according to the disclosure. The small diameter portion 124 is positioned at a proximal end of the tube main body 121A, and is formed into a cylindrical shape having a smaller outer diameter than the outer diameter of the large diameter portion 123.

The connection portion 125 is a tube body which connects the large diameter portion 123 and the small diameter portion 124.

Further, in a state in which the tube 12A is assembled for the oscillator unit 11, a whole of the tube 12A is positioned in an inner side of the oscillator unit 11.

An inner peripheral surface of the tube main body 121A has the same shape as the inner peripheral surface of the tube main body 121 described in the first embodiment mentioned above.

Here, all the sets of second wiring patterns 132 are formed, as illustrated in FIG. 10, so as to extend to the proximal end side from the outer peripheral surface 12b of the flange portion 122 and extend to an outer peripheral surface 12g of the small diameter portion 124 through an outer peripheral surface 12e of the large diameter portion 123 and an outer peripheral surface 12f of the connection portion 125. Further, all the FPC boards 135 are respectively stuck on the outer peripheral surface 12g of the small diameter portion 124 and are electrically connected to all the sets of second wiring patterns 132.

According to the present second embodiment described above, the following effects can be achieved in addition to the same effects as those of the first embodiment mentioned above.

In the ultrasound transducer 10A according to the present second embodiment, the proximal end of the tube 12A is provided with the small diameter portion 124 having an outer size smaller than the other regions. Further, the signal line SL is electrically connected to the second wiring pattern 132 on the outer peripheral surface 12g of the small diameter portion 124. As a result, it is not necessary to make the stuck area protrude to the proximal end side from the proximal end of the oscillator unit 11 taking into consideration the thickness of the stuck FPC board 135. More specifically, a whole of the tube 12A can be positioned in the inner side of the oscillator unit 11.

Therefore, on the basis of the ultrasound transducer 10A according to the present second embodiment, it is possible to preferably achieve an effect of shortening the length of the tube 12A and shortening the rigid length.

Further, since the FPC board 135 is stuck to the outer peripheral surface 12g of the small diameter portion 124, the diameter of the tube 12A in the proximal end side can be set to a small state even in a state in which the FPC board 135 is stuck. As a result, the proximal end side of the tube 12A can be inserted into the oscillator unit 11 after the FPC board 135 is stuck to the outer peripheral surface 12g of the small diameter portion 124. In other words, the FPC board 135 can be stuck to the outer peripheral surface 12g of the small diameter portion 124 in a state of having no oscillator unit 11. More specifically, it is possible to reduce difficulty for the sticking work and reduce a manufacturing cost.

Third Embodiment

Next, a description will be given of the present third embodiment.

In the following description, same reference signs are attached to the same structures as those of the first embodiment mentioned above, and a detailed description thereof will be omitted or simplified.

Figure 11:
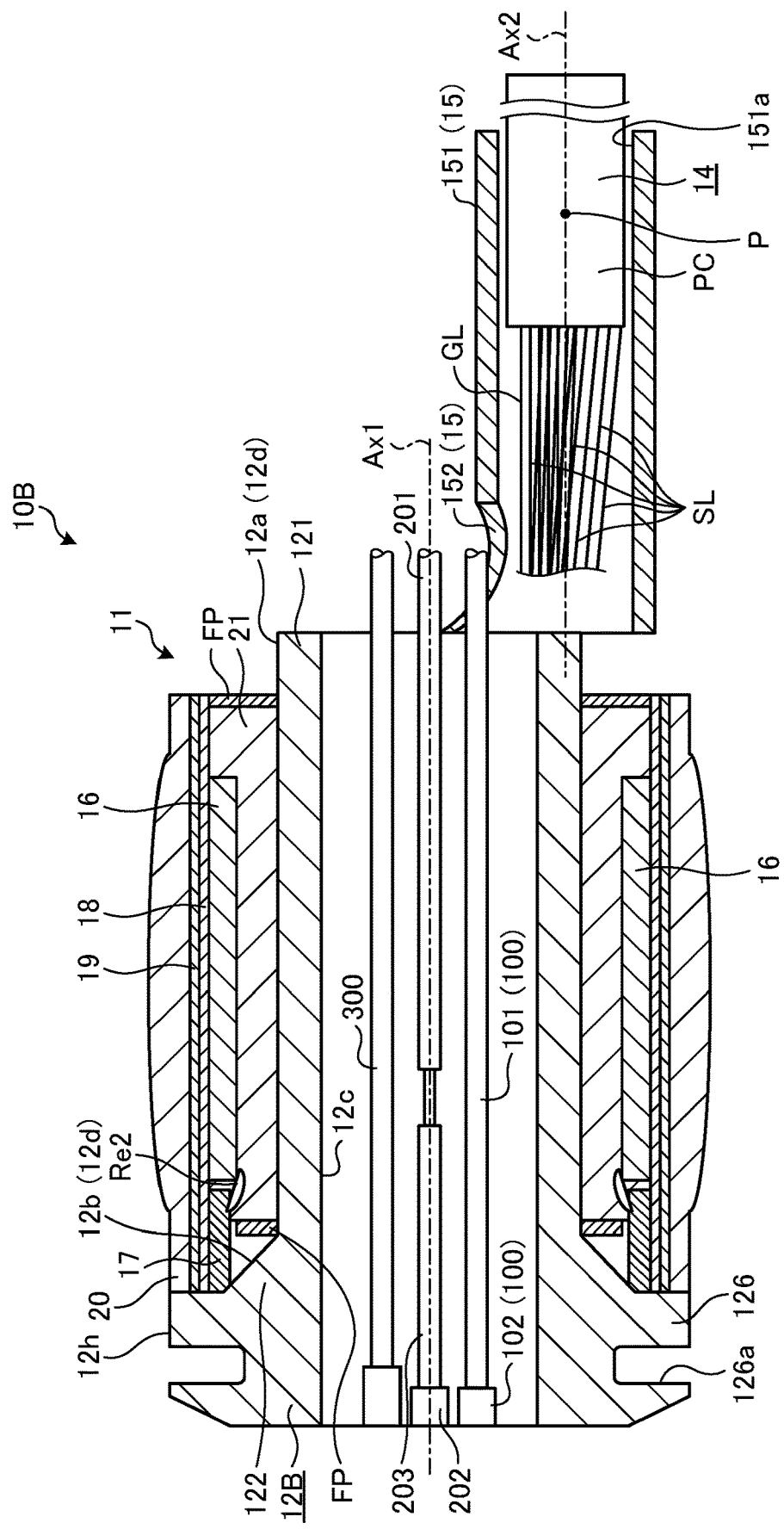
FIG. 11 is a view illustrating a structure of an ultrasound transducer according to a third embodiment.

FIG. 11 is a view illustrating a structure of an ultrasound transducer 10B according to the present third embodiment. Specifically, FIG. 11 is a cross sectional view corresponding to FIG. 3. In FIG. 11, an illustration of the first and second electrodes 22 and 23, the groove unit for short circuit 181, the conductive resin Re1, the first and second conductive layers 172 and 173, and the first and second wiring patterns 131 and 132 is omitted for convenience of description.

The ultrasound transducer 10B according to the present third embodiment employs a tube 12B having a different shape from the tube 12 for the ultrasound transducer 10 (FIG. 3) described in the first embodiment mentioned above, as illustrated in FIG. 11.

In the tube 12B, a balloon locking unit 126 is added to the tube 12 described in the first embodiment mentioned above, as illustrated in FIG. 11.

The balloon locking unit 126 is integrally formed in the distal end of the flange portion 122, and is formed into a cylindrical shape having a greater outer diameter than the maximum diameter of the outer peripheral surface 12b of the flange portion 122. An inner diameter of the balloon locking unit 126 is set to be identical to the inner diameters of the tube main body 121 and the flange portion 122. Further, a groove portion 126a which can lock a distal end side of a balloon capable of filling with an ultrasound wave medium is formed in an outer peripheral surface 12h of the balloon locking unit 126. A specific illustration of the proximal end side of the balloon is omitted, however, the proximal end side is locked by a balloon locking member which is a different member from the tube 12B.

According to the present third embodiment mentioned above, the following effects can be achieved in addition to the same effects as those of the first embodiment mentioned above.

In the ultrasound transducer 10B according to the present third embodiment, the groove portion 126a to which the balloon is locked is formed in the outer peripheral surface 12h in the distal end of the tube 12B. As a result, in comparison with the case where the tube and the balloon locking unit are constructed separately, it is possible to omit an assembling work of the tube and the balloon locking unit, and it is possible to reduce a manufacturing cost.

Other Embodiments

The description is given of the modes for carrying out the disclosure, however, the disclosure is not limited to the first to third embodiments mentioned above.

In the first to third embodiments mentioned above, the FPC board 135 may be omitted and the signal line SL may be electrically connected directly to the second wiring pattern 132 as long as the signal line SL is routed toward the fixed position P from the area Ar.

In the first to third embodiment mentioned above, the bent portion 134 is bent perpendicularly from the end portion of the pattern main body 133 and extends, however, may be structured such as to be bent at the other angles and extend. Further, the second wiring pattern 132 may be constructed only by the pattern main body 133 while omitting the bent portion 134.

In the first to third embodiments mentioned above, the endoscope system 1 has both of the function of generating the ultrasound image and the function of generating the endoscope image, however, may be structured so as to have only the function of generating the ultrasound image without being limited thereto.

In the first to third embodiments mentioned above, the endoscope system 1 may be constructed as an endoscope system which observes an internal portion of a subject such as a machine structure in an industrial field without being limited to the medical field.

According to the ultrasound transducer and the ultrasound endoscope of the disclosure, it is possible to achieve an effect of making a rigid length short.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer comprising:
   a tube formed of an insulating material, the tube having an outer peripheral surface including an outer proximal peripheral surface at a proximal end of the tube;
   a transducer cable having a distal end fixed proximally relative to the proximal end of the tube, a central axis of the transducer cable being offset radially from a central axis of the tube such that the distal end of the transducer cable is fixed at a radial side of the tube offset from the central axis of the tube;
   a plurality of piezoelectric elements arranged circumferentially around the outer peripheral surface of the tube, each piezoelectric element of the plurality of piezoelectric elements being configured to output an ultrasound wave according to an electric signal input from the transducer cable, and to convert an ultrasound wave input from an external portion into an electric signal; and
   a plurality of relays electrically connected respectively to a plurality of signal lines included in the transducer cable and to the plurality of piezoelectric elements, the plurality of relays being configured to respectively electrically connect the plurality of signal lines to the plurality of piezoelectric elements,
   wherein the plurality of signal lines are respectively electrically connected to proximal ends of the plurality of relays on the outer peripheral surface of the tube,
   the proximal ends of the plurality of relays being arranged in a partial area corresponding to the outer proximal peripheral surface on the radial side of the tube, and
   the outer peripheral surface of the tube opposes an inner peripheral surface of the plurality of piezoelectric elements in a radial direction of the tube.

2. The ultrasound transducer according to claim 1, wherein the proximal ends of the plurality of relays each include an extended portion which extends to the radial side of the tube from the outer proximal peripheral surface of the tube.

3. The ultrasound transducer according to claim 2, wherein each of the plurality of relays include:
   a wiring pattern provided on the outer peripheral surface of the tube, the wiring pattern being electrically connected to a respective piezoelectric element of the plurality of piezoelectric elements; and
   each of the extended portions are formed on one or more flexible boards attached on the outer proximal peripheral surface of the tube.

4. The ultrasound transducer according to claim 3, wherein the one or more flexible boards comprises a plurality of flexible boards, each having a first portion extending along a circumferential direction of the tube and a second portion bent relative to the circumferential direction, the second portion extending to the radial side of the tube.

5. The ultrasound transducer according to claim 4, wherein at least the second portion of the plurality of flexible boards overlap each other in a radial direction of the tube.

6. The ultrasound transducer according to claim 3, wherein:
the outer peripheral surface of the tube is cylindrical,
wherein each wiring pattern includes:
a main body extending along the central axis of the tube; and
a bent portion being bent relative to the main body, the bent portion extending toward the partial area from an end of the main body, an end of the bent portion being electrically connected to the one or more flexible boards, and
wherein the ends of the bent portions corresponding to the plurality of relays are arranged longitudinally along a central axis direction of the tube.

7. The ultrasound transducer according to claim 3, wherein the tube includes:
a tube main body having the outer peripheral surface; and
a flange protruding from the outer peripheral surface, the flange facing the plurality of piezoelectric elements in a direction along the central axis of the tube,
wherein the wiring patterns are provided across the outer peripheral surface and on at least a portion of a surface of the flange, and
wherein a pitch angle around the central axis of the tube of a plurality of distal ends electrically connected respectively to the plurality of piezoelectric elements in the plurality of wiring patterns is set to be identical to a pitch angle around a central axis of the plurality of piezoelectric elements.

8. The ultrasound transducer according to claim 1, wherein the proximal end of the tube is provided with a stepped portion having a smaller outer size than other portions of the tube,
wherein the plurality of signal lines are electrically connected to the proximal ends of the plurality of relays on an outer peripheral surface of the stepped portion, and
wherein at least a part of the stepped portion is positioned in an inner side of a tubular shape formed by the plurality of piezoelectric elements.

9. The ultrasound transducer according to claim 1, wherein the tube includes a groove configured to attach a balloon, the groove being formed on the outer peripheral surface of a distal end of the tube.

10. The ultrasound transducer according to claim 1, wherein the plurality of relays include a plurality of respective distal ends electrically connected to the respective plurality of piezoelectric elements, the plurality of relays being configured such that a distal arranging direction of the distal ends of the plurality of relays is different from a second arranging direction of the plurality of the proximal ends of the plurality of relays.

11. An ultrasound endoscope comprising:
the ultrasound transducer according to claim 1;
an objective optical portion inserted into an inner portion of the tube, the objective optical portion being configured to take in a subjective image; and
a light guide inserted into the inner portion of the tube, the light guide being configured to guide an illumination light that irradiates a subject.

12. The ultrasound transducer according to claim 1, wherein the plurality of relays comprises a plurality of first relays, the ultrasound transducer further comprising one or more second relays electrically connected to a common ground line in the transducer cable and to the plurality of piezoelectric elements.

13. The ultrasound transducer according to claim 12, wherein the one or more second relays at least partially extend along an inner peripheral surface of the tube.

14. The ultrasound transducer according to claim 13, further comprising a printed board having a plurality of first conductive layers and one or more second conductive layers, each of the plurality of first conductive layers being electrically isolated from each other and from the one or more second conductive layers, the plurality of first conductive layers electrically connecting a signal electrode on each of the plurality of piezoelectric elements to a respective first distal end of the plurality of first relays and the one or more second conductive layers electrically connecting a ground electrode on each of the plurality of piezoelectric elements to a second distal end of the one or more second relays.

15. The ultrasound transducer according to claim 14, wherein:
the printed board having a first sloped surface relative to the central axis of the tube, the plurality of first conductive layers being formed on a first portion of the first sloped surface, the one or more second conductive layers being formed on a second portion of the first sloped surface;
the tube comprising a tube main body having the outer peripheral surface and a flange protruding from the outer peripheral surface, the flange having a second sloped surface relative to the central axis of the tube and facing the first sloped surface;
the first distal ends of the plurality of first relays are disposed on the second sloped surface to respectively electrically connect to the plurality of first conductive layers on the first portion of the first sloped surface; and
the second distal ends of the one or more second relays are disposed on the second sloped surface and configured to respectively electrically connect to the one or more second conductive layers on the second portion of the first sloped surface.

* * * * *